United States Patent
Ishihara et al.

(10) Patent No.: US 8,853,426 B2
(45) Date of Patent: Oct. 7, 2014

(54) METHOD FOR MANUFACTURING ESTER

(75) Inventors: Kazuaki Ishihara, Nagoya (JP); Muhammet Uyanik, Nagoya (JP)

(73) Assignee: National University Corporation Nagoya University, Nagoya-Shi (JP)

( * ) Notice: Subject to any disclaimer, the term of this patent is extended or adjusted under 35 U.S.C. 154(b) by 0 days.

(21) Appl. No.: 13/881,544

(22) PCT Filed: Oct. 11, 2011

(86) PCT No.: PCT/JP2011/073340
§ 371 (c)(1),
(2), (4) Date: Apr. 25, 2013

(87) PCT Pub. No.: WO2012/060185
PCT Pub. Date: May 10, 2012

(65) Prior Publication Data
US 2013/0217898 A1    Aug. 22, 2013

(30) Foreign Application Priority Data

Nov. 2, 2010  (JP) ................. 2010-245944

(51) Int. Cl.
| | | |
|---|---|---|
| C07D 313/16 | (2006.01) | |
| C07B 33/00 | (2006.01) | |
| C07D 307/83 | (2006.01) | |
| C07D 309/30 | (2006.01) | |
| C07D 313/04 | (2006.01) | |
| C07D 307/935 | (2006.01) | |
| C07D 323/04 | (2006.01) | |
| C07D 307/33 | (2006.01) | |
| C07D 307/77 | (2006.01) | |
| C07D 307/88 | (2006.01) | |
| C07D 307/79 | (2006.01) | |

(52) U.S. Cl.
CPC .............. *C07D 313/04* (2013.01); *C07B 33/00* (2013.01); *C07D 307/83* (2013.01); *C07D 309/30* (2013.01); *C07D 307/935* (2013.01); *C07D 323/04* (2013.01); *C07D 307/33* (2013.01); *C07D 307/77* (2013.01); *C07D 307/88* (2013.01); *C07D 307/79* (2013.01)
USPC ...................................................... 549/272

(58) Field of Classification Search
None
See application file for complete search history.

(56) References Cited

FOREIGN PATENT DOCUMENTS

| JP | A 9-104681 | 4/1997 |
| JP | A 2003-190804 | 7/2003 |
| JP | A 2004-352636 | 12/2004 |

OTHER PUBLICATIONS

Nakajima et al Proc. 91st Annual Mtg, Chem. Soc, Japan Mar. 11, 2011.*

Neimann et al; "Electrophilic Activation of Hydrogen Peroxide: Selective Oxidation Reactions in Perfluorinated Alcohol Solvents;" Organic Letters; 2000; vol. 2; No. 18; pp. 2861-2863.

Berkessel et al; "Efficient catalytic methods for the Baeyer-Villiger oxidation and epoxidation with hydrogen peroxide;" Tetrahedron Letters; 2001; vol. 42; pp. 2293-2295.

Berkessel et al; "Baeyer-Villiger Oxidations with Hydrogen Peroxide in Fluorinated Alcohols: Lactone Formation by a Nonclassical Mechanism;" Angew. Chem. Intl. Ed.; 2002; vol. 41; No. 23; pp. 4481-4484.

Brink et al; "Selenium-Catalyzed Oxidations with Aqueous Hydrogen Peroxide. 2. Bayer-Villiger Reactions in Homogenous Solution;" Journal of Organic Chemistry; 2001; vol. 66; pp. 2429-2433.

Ichikawa et al; "Synthesis of novel organoselenium as catalyst for Bayer-Villiger oxidation with 30% $H_2O_2$;" Tetrahedron Letters; 2005; vol. 46; pp. 8665-8668.

Hao et al; "Green Baeyer-Villiger oxidation with hydrogen peroxide: $SN[N(SO_2C_8F_{17})_2]_4$ as a highly selective Lewis acid catalyst in a fluorous biphase system;" The Royal Society of Chemistry; *Green Chemistry*; 2003; vol. 5; pp. 524-528.

Pillai et al; "Sn-exchanged hydrotalcites as catalysts for clean and selective Baeyer-Villiger oxidation of ketones using hydrogen peroxide;" Journal of Molecular Catalysis A: Chemical; 2003; vol. 191; pp. 93-100.

Llamas et al; Heterogenous Baeyer-Villiger oxidation of ketones with $H_2O_2$/nitrile, using Mg/Al hydrotalcite as catalyst; Tetrahedron; 2007; vol. 63; pp. 1435-1439.

Llamas et al; "Environmentally friendly Baeyer-Villiger oxidation with $H_2O_2$/nitrile over $Mg(OH)_2$ and MgO;" Applied Catalysis B: Environmental; 2007; vol. 72; pp. 18-25.

Chen; et al; "The Catalytic Baeyer-Villiger Oxidation of Cyclohexanone to ϵ-Caprolactone over Stibium-containing Hydrotalcite;" Catal Lett; 2009; vol. 131; pp. 618-623.

Dauben et al; "Silicon-Directed Baeyer-Villiger Reactions. Stereospecific Synthesis of Olefinic Acids and Esters;" Journal of the American Chemical Society; 1980; vol. 102; pp. 6894-6896.

Inokoishi et al; "A New Powerful Strategy for the Organocatalytic Asymmetric Construction of a Quaternary Carbon Stereogenic Center;" Organic Letters; 2010; vol. 12; No. 7; pp. 1616-1619.

Fujiki et al; "Evaluation of Lewis Acidity of 'Naked' Lithium Ion through Diels-Alder Reaction Catalyzed by Lithium TFPB in Nonpolar Organic Solvents;" Chemistry Letters; 2000; vol. 29; pp. 62-63.

(Continued)

Primary Examiner — Heidi Reese

(74) Attorney, Agent, or Firm — Oliff PLC

(57) ABSTRACT

The present invention relates to a method for manufacturing an ester from a ketone or an aldehyde, which is a reactive substrate, by a Baeyer-Villiger oxidation reaction using hydrogen peroxide, and in this method, as a catalyst, M$(BAr_4)_n$, which is a metal borate, is used (M represents an alkali metal or an alkaline earth metal; Ar represents an aryl; and n is the same number as the valence of M). For example, when cyclohexanone was used as the reactive substrate, and $Sr[B(3,5-CF_3C_6H_3)_4]_2$ was used as the catalyst, ϵ-caprolactone was obtained at an isolated yield of 82%.

9 Claims, No Drawings

(56) References Cited

OTHER PUBLICATIONS

Liao et al; "An Efficient Preparation of Bis(indole)methanes Catalyzed by Tetrakis[3,5-bis(trifluoromethyl)phenyl]borate Salts in Aqueous Medium;" Synthesis; 2007; No. 20; pp. 3125-3128.

Nakajima et al; "Alkali or Alkaline Earth Metal Bulky Borate Salt Catalysis for Baeyer-Villiger Oxidation with Hydrogen Peroxide;" 91st Annual Meeting of the Chemical Society of Japan in Spring (2011); Koen Yokoshu IV; Mar. 11, 2011; p. 1221.

Nakajima et al; "Environmental harmony type catalytic Baeyer-Villiger oxidation reaction using hydrogen peroxide water as an oxidant;" Dai 41 Kai Annual Meeting of Union Chemistry-Related Societies in Chubu Area; Japan Koen Yokoshu; Nov. 6, 2010; p. 199 (with partial translation).

Jan. 17, 2012 Search Report issued in International Patent Application No. PCT/JP2011/073340 (with translation).

May 14, 2013 International Preliminary Report on Patentability issued in International Patent Application No. PCT/JP2011/073340 (with translation).

Mar. 18, 2014 Search Report issued in European Patent Application No. 11 83 7836.3.

Pande et al., "Phase Transfer Catalyzed Oxidation of Ketones with Borax-$H_2O_2$," Montashefte Fur Chemise, vol. 126, Jan. 1, 1995, pp. 647-652.

\* cited by examiner

METHOD FOR MANUFACTURING ESTER

TECHNICAL FIELD

The present invention relates to a method for manufacturing an ester, and more particularly relates to a method for manufacturing an ester by a Baeyer-Villiger oxidation reaction.

BACKGROUND ART

A Baeyer-Villiger oxidation reaction has been widely used in organic synthetic fields as a method for converting a ketone or an aldehyde into a useful ester (including a lactone, which is a cyclic ester). For example, ε-caprolactone obtained from cyclohexanone is useful as a raw material for a polyester and a polyamide, and development of an efficient synthetic method of ε-caprolactone is important. Since a Baeyer-Villiger oxidation reaction of cyclohexanone is a ring expansion reaction from a stable six-membered ring with a small ring strain to an unstable seven-membered ring with a large ring strain, in general, it has been believed that this reaction is difficult to perform because of low reactivity. Hence, an organic peroxide having a strong oxidizing power has been frequently used. However, various problems, such as explosive properties and chemical selectivity of the organic peroxide, cost for oxidation reaction, and waste liquid treatment methods, have not been solved. On the other hand, hydrogen peroxide water is a safe and inexpensive oxidant and is also regarded as an ideal oxidant because water is only produced as a by-product. A catalytic method using hydrogen peroxide water as an oxidant has also been reported. Four representative methods will be described below.

As a first method, a method may be mentioned in which TsOH is used as the catalyst in a HFIP (1,1,1,3,3,3-hexafluoro-2-propanol) solvent (for example, see Non Patent Literatures 1 and 2). As a second method, a method may be mentioned in which an organic selenium reagent is used as the catalyst (for example, see Non Patent Literatures 4 and 5). As a third method, a method may be mentioned in which a tin complex of perfluoroalkane sulfonic acid is used as a Lewis acid catalyst in a fluorous biphase system (for example, see Non Patent Literature 6 and Patent Literature 1). As a fourth method, a heterogeneous oxidation method may be mentioned in which a hydrotalcite solid catalyst containing Mg, Mg—Al, Sn, and/or the like is used (for example, see Non Patent Literatures 7 to 10).

CITATION LIST

Patent Literature

Patent Document 1: JP2003-190804A

Non-Patent Literature

Non-Patent Document 1: Organic Letters, 2000, vol. 2, p 2861
Non-Patent Document 2: Tetrahedron Letters, 2001, vol. 42, p 2293
Non-Patent Document 3: Angew. Chem. Int. Ed., 2002, vol. 41, p 4481
Non-Patent Document 4: J. Org. Chem., 2001, vol. 66, p 2429
Non-Patent Document 5: Tetrahedron Letters, 2005, vol. 46, p 8665
Non-Patent Document 6: Green Chem., 2003, vol. 5, p 524
Non-Patent Document 7: J. Mol. Catal. A: Chem., 2003, vol. 191, p 93
Non-Patent Document 8: Tetrahedron, 2007, vol. 63, p 1435
Non-Patent Document 9: App. Catal. B: Environ., 2007, vol. 72, p 18
Non-Patent Document 10: Catal. Lett., 2009, vol. 131, p 618

DISCLOSURE OF INVENTION

However, in the first method, since epoxidation of an olefin was also facilitated, there has been a problem in that the functional group selectivity was not excellent when a cyclic ketone containing an olefin was used as a reactive substrate. In addition, in the second method, there has been a problem in that the organic selenium reagent used as the catalyst had high toxicity; in the third method, there has been a problem in that the yield of ε-caprolactone obtained from cyclohexanone was low; and in the fourth method, there has been a problem in that the substrate generality was not satisfactory.

The present invention was made to solve the problems as described above, and a primary object of the present invention is to obtain an ester (including a lactone) from a ketone or an aldehyde at a high yield using a low-toxic catalyst.

In order to achieve the above object, the present inventors first discovered that a borate salt ($M(BAr_4)_n$; M=Li, Na, Ca, Sr, or the like) of a low-toxic or a non-toxic alkali metal or alkaline earth metal shows excellent catalytic activity in a Baeyer-Villiger oxidation reaction of a ketone or an aldehyde using hydrogen peroxide, and as a result, the present invention was made.

That is, a method for manufacturing an ester of the present invention is a method for manufacturing an ester from a ketone or an aldehyde, which is a reactive substrate, by a Baeyer-Villiger oxidation reaction using hydrogen peroxide, wherein $M(BAr_4)_n$, which is a borate salt, is used as a catalyst (M represents an alkali metal, an alkaline earth metal, or a triarylmethyl; four Ar's each represent an aryl having an electron withdrawing group and are identical to or different from each other; and n is the same number as the valence of M).

According to the method for manufacturing an ester of the present invention, an ester can be obtained at a high yield from a ketone or an aldehyde, which is a reactive substrate, using a low-toxic catalyst. In addition, since hydrogen peroxide is used instead of an organic peroxide, water is the only by-product derived from the peroxide, and hence this Baeyer-Villiger oxidation reaction may be regarded as an environmental friendly reaction. Furthermore, when a cyclic ketone is used as the reactive substrate, oxidation reaction thereof efficiently progresses under mild conditions, and as a result, a lactone can be obtained at a high yield.

BEST MODES FOR CARRYING OUT THE INVENTION

A method for manufacturing an ester of the present invention is a method for manufacturing an ester from a ketone or an aldehyde, which is a reactive substrate, by a Baeyer-Villiger oxidation reaction using hydrogen peroxide, wherein $M(BAr_4)_n$, which is a borate salt, is used as a catalyst (M represents an alkali metal, an alkaline earth metal, or a triarylmethyl; four Ar's each represent an aryl having an electron withdrawing group and are identical to or different from each other; and n is the same number as the valence of M).

In the method for manufacturing an ester of the present invention, M of $M(BAr_4)_n$, which is the borate salt, represents an alkali metal, an alkaline earth metal, or a triarylmethyl. As the alkali metal, for example, Li, Na, and K may be mentioned, and as the alkaline earth metal, for example, Mg, Ca, Sr, and Ba may be mentioned. Three aryls of the triarylmethyl may be identical to or different from each other. When the three aryls are different, all of them may be independently different from each other, or two of the three aryls may be identical to each other and the remaining aryl may be different therefrom. As the triarylmethyl, for example, triphenylmethyl (trityl) and tris(pentafluorophenyl)methyl may be mentioned. In addition, when M represents an alkali metal or a triarylmethyl, n indicates 1, and when M represents an alkaline earth metal, n indicates 2. Four Ar's are each an aryl having an electron withdrawing group and may be identical to or different from each other. When the four aryls are different, all of them may be independently different from each other: two of the four aryls may be identical to each other and the remaining two thereof may be different from each other; two of the four aryls may be identical to each other and the remaining two thereof may also be identical to each other; and three of the four aryls may be identical to each other. As the electron withdrawing group, for example, a halogen atom, a trihalomethyl group, a nitro group, and a nitrile group may be mentioned. As the halogen atom, a fluorine atom is preferable, and as the trihalomethyl group, a trifluoromethyl group is preferable. In addition, as the aryl having an electron withdrawing group, for example, a pentafluorophenyl group and 3,5-bis(trifluoromethyl)phenyl group are preferable.

In the method for manufacturing an ester of the present invention, the amount of $M(BAr_4)_n$, which is the borate salt, is not particularly limited as long as it is a catalytic amount and is, for example, preferably 0.01 to 20 percent by mole with respect to that of the reactive substrate. When the amount is less than 0.01 percent by mole, it is not preferable since problems, such as a decrease in reaction rate and an increase in ratio of by-products, occur, and even when the amount is more than 20 percent by mole, since the yield is not remarkably increased thereby, it is not preferable from an economical point of view. In consideration of a promotion effect of the reaction rate, the amount of the borate salt is preferably set lower limit to 0.1 percent by mole with respect to that of the reactive substrate. In addition, from an economical point of view, an amount of 5 percent by mole with respect to that of the reactive substrate is more preferably set to the upper limit.

In the method for manufacturing an ester of the present invention, although the ketone to be used as the reactive substrate is not particularly limited, for example, a cyclic ketone, a chain ketone, and a chromanone may be mentioned. As the cyclic ketone, for example, besides a cyclopropanone, a cyclobutanone, a cyclopentanone, a cyclohexanone, and a cycloheptanone, a condensed ring ketone and the like may also be mentioned. When the cyclic ketone mentioned above is used as the reactive substrate, a lactone is obtained as a reaction product. In general, since a cyclohexanone is stable due to its small ring strain, it has been believed that a Baeyer-Villiger oxidation reaction to form ε-caprolactone, which has a large ring strain and which is unstable, is not likely to progress; however, according to the method for manufacturing an ester of the present invention, the reaction progresses at a high yield. In addition, as the cyclic ketone, besides those mentioned above, for example, when synthetic intermediates of natural products, synthetic intermediates of medicines and agrichemicals, monomers for forming polymers, and the like each have a cyclic ketone skeleton as a partial structure thereof, the synthetic intermediates and the monomers may also be used as the reactive substrates. As the chain ketone, for example, there may be mentioned a dialkyl ketone such as dipentyl ketone, an aryl alkyl ketone such as acetophenone, or a diaryl ketone such as benzophenone. As the chromanone, for example, there may be mentioned 4-chromanone and 3-chromanone. In addition, as the aldehyde to be used as the reactive substrate, for example, aromatic aldehydes, such as benzaldehyde, 4-chlorobenzaldehyde, and 1-naphtylaldehyde, may be mentioned. Those reactive substrates mentioned above may have a carbon-carbon double bond (that is, an olefinic bond), a carbon-carbon triple bond, a halogen group, a hydroxy group, a silyl group, or a siloxy group. Although the olefin may be converted into an epoxy by hydrogen peroxide in some cases, the probability of this conversion is low in the method for manufacturing an ester of the present invention, and the ester is selectively produced. As the reactive substrate having an olefinic bond, for example, a ketone or an aldehyde, each having a vinyl group, an aryl group, an isopentyl group, or the like, may be mentioned. As the reactive substrate having a carbon-carbon triple bond, for example, a ketone or an aldehyde, each having an ethynyl group, a propionyl group, or the like, may be mentioned. As the reactive substrate having a silyl group, for example, a ketone or an aldehyde, each having a trimethylsilyl group, a dimethylphenylsilyl group, a dimethyl-t-butylsilyl group or the like, may be mentioned. As the reactive substrate having a siloxy group, for example, a ketone or an aldehyde, each having a trimethylsiloxy group, a dimethylphenylsiloxy group, a dimethyl(t-butyl)siloxy group or the like, may be mentioned.

In the method for manufacturing an ester of the present invention, a reaction solvent may be appropriately selected in accordance with the reactive substrate and/or the catalyst, and for example, a halogenated hydrocarbon, an aromatic hydrocarbon, a nitrile-based solvent, an ester-based solvent, and a mixture containing at least two of the above solvents may be mentioned. In addition, depending on the types of reactive substrate and catalyst, a mixed solvent containing water and at least one of the above exemplified solvents may also be used. As the halogenated hydrocarbon, for example, 1,2-dichloroethane (DCE) and 1,4-dichlorobutane (DCB) may be mentioned; as the aromatic hydrocarbon, for example, toluene, xylene, and benzene may be mentioned; as the nitrile-based solvent, for example, acetonitrile, propionitrile, and butyronitrile may be mentioned; and as the ester-based solvent, for example, methyl acetate and ethyl acetate may be mentioned.

In the method for manufacturing an ester of the present invention, a reaction temperature may be appropriately set in accordance with the reactive substrate and/or the catalyst. An excessively low reaction temperature is not preferable since the time required to complete the reaction may become longer due to a decrease in reaction rate, and on the other hand, an excessively high reaction temperature is also not preferable since the reactive substrate may be decomposed and/or a side reaction may become dominant in some cases. Accordingly, an appropriate reaction temperature may be changed depending on the reactive substrate and/or the catalyst. Hence, although a preferable range of the reaction temperature may not be simply determined, as one guideline thereof, an appropriate range may be set in a range of 0° C. to 100° C. and preferably in a range of 25° C. (room temperature) to 70° C.

In the method for manufacturing an ester of the present invention, as a promoter, a Brønsted acid may also be used. When the Brønsted acid is used as the promoter with the borate salt catalyst, the reaction activity is further improved. As the promoter described above, for example, a phenol having at least one OH group on its aromatic ring, a carboxylic acid, an oxocarbonic acid, a phosphate monoester, or a phosphate diester may be mentioned. As the phenol, for example, pentafluorophenol, catechol, 3-fluorocatechol, tetrafluorocatechol, tetrachlorocatechol, resorcinol, 4-fluororesorcinol, tetrafluororesorcinol, or tetrachlororesorcinol may be mentioned. As the carboxylic acid, for example, acetic acid, mandelic acid, oxalic acid, malonic acid, succinic acid, salicylic acid, or phthalic acid may be mentioned. As the oxocarbonic acid, for example, deltic acid, squaric acid, croconic acid, rhodizonic acid, or heptagonic acid may be mentioned. As the phosphate monoester or diester, for example, there may be mentioned binaphthyl hydrogen phosphate (BP). Among those mentioned above, since having a high reaction promotion effect, tetrafluorocatechol and oxalic acid are preferable. Furthermore, in consideration of inexpensive price, oxalic acid is preferable.

In the method for manufacturing an ester of the present invention, for example, the amount of the promoter with respect to that of the reactive substrate is preferably 0.01 to 100 percent by mole. In addition, the amount of the promoter is preferably 1 to 10 times and more preferably 1 to 5 times in mole that of the borate salt.

It is apparent that the present invention is not limited to the above-described embodiment at all and various embodiments can be made within the technical scope of the present invention.

EXAMPLES

In the following Examples and Comparative Examples, $^1$H NMR spectrum was measured by an ECS-400 (400 MHz) spectrometer manufactured by JEOL, and $^{13}$C NMR spectrum was measured by an ECS-400 (100 MHz) spectrometer manufactured by JEOL. The progress of reaction was monitored by thin-layer chromatography (TLC) using a precoated TLC plate (silica gel 60 GF254, 0.25 mm) manufactured by Merck. As solvents and reagents for the reaction, commercially available products were used without any additional treatment.

Reference Example

Borate salts functioning as catalysts used in the following Examples and Comparative Examples will be described. As $NaB(3,5-CF_3C_6H_3)_4$, $LiB(C_6F_5)_4$, and $Ph_3CB(C_6F_5)_4$, commercially available products were used for the reaction without any additional treatment. $LiB(3,5-CF_3C_6H_3)_4$ and $KB(3,5-CF_3C_6H_3)_4$ were synthesized in accordance with methods described in the literature (Organomet., 1992, vol. 11, p 3920).

$Sr[B(3,5-CF_3C_6H_3)_4]_2 \cdot 10H_2O$ was synthesized as described below. That is, after $SrCl_2 \cdot 6H_2O$ (1.33 g, 5 mmol) was added to a mixed liquid of $LiB(3,5-CF_3C_6H_3)_4 \cdot 4H_2O$ (470 mg, 0.5 mmol), $Et_2O$ (5 ml), and purified water (5 ml), stirring was performed at room temperature for 2 days. After the reaction was completed, a water layer was extracted with $Et_2O$, and an organic layer thus obtained was washed 5 times with purified water. After the solvent was removed by an evaporator, a solid thus obtained was thoroughly washed with purified water and hexane, so that $Sr[B(3,5-CF_3C_6H_3)_4]_2 \cdot 10H_2O$ was obtained (435 mg, 0.22 mmol, yield: 87% (calculated based on the borate).

In addition, $Ca[B(3,5-CF_3C_6H_3)_4]_2 \cdot 8H_2O$ and $Ba[B(3,5-CF_3C_6H_3)_4]_2 \cdot 7H_2O$ were synthesized in a manner similar to that for $Sr[B(3,5-CF_3C_6H_3)_4]_2 \cdot 10H_2O$ except that $CaCl_2$ and $BaCl_2$ were used, respectively, instead of using $SrCl_2$. Furthermore, $Sr[B(C_6F_5)_4]_2$ was synthesized in a manner similar to that for $Sr[B(3,5-CF_3C_6H_3)_4]_2 \cdot 10H_2O$ except that $LiB(C_6F_5)_4$ was used instead of using $LiB(3,5-CF_3C_6H_3)_4 \cdot 4H_2O$.

The appearance and spectral data of the synthesized borate salts are shown below.

$LiB(3,5-CF_3C_6H3)_4$

White powder. $^1$H NMR ($CD_3CN$, 400 MHz) δ 7.65-7.70 (m, 12H); $^{13}$C NMR ($CD_3CN$, 100 MHz) δ118.7, 125.5 (q, $J_{C-F}$=270 Hz), 129.9 (q, $J_{C-F}$=31.5 Hz), 135.7, 162.6 (q, $J_{B-C}$=49.6 Hz); $^{19}$F NMR ($CD_3CN$) δ−63.1. Anal. Calcd. for $C_{32}H_{20}BF_{24}LiO_4$: C, 40.79; H, 2.14. Found: C, 41.00; H, 1.88.

$KB(3,5-CF_3C_6H3)_4$

White powder. $^1$H NMR ($CD_3CN$, 400 MHz) δ 7.65-7.70 (m, 12H); $^{13}$C NMR ($CD_3CN$, 100 MHz) δ118.7, 125.5 (q, $J_{C-F}$=271 Hz), 130.0 (q, $J_{C-F}$=32.4 Hz), 135.7, 162.7 (q, $J_{B-C}$=49.6 Hz); $^{19}$F NMR ($CD_3CN$) δ−63.1. Anal. Calcd. for $C_{32}H_{16}BF_{24}LiO_2$: C, 40.96; H, 1.72. Found: C, 41.01; H, 1.70.

$Sr[B(3,5-CF_3C_6H_3)_4]_2 \cdot 10H_2O$

White powder. $^1$H NMR ($CD_3CN$, 400 MHz) δ7.65-7.70 (m, 24H); $^{13}$C NMR ($CD_3CN$, 100 MHz) δ118.7, 125.5 (q, $J_{C-F}$=271 Hz), 129.9 (q, $J_{C-F}$=31.5 Hz), 135.7, 162.7 (q, $J_{B-C}$=49.6 Hz); $^{19}$F NMR ($CD_3CN$) δ−63.1. Anal. Calcd. For $C_{64}H_{44}BF_{48}O_{10}Sr$: C, 38.55; H, 2.22. Found: C, 38.56; H, 2.13.

$Ca[B(3,5-CF_3C_6H_3)_4]_2 \cdot 8H_2O$

White powder. $^1$H NMR ($CD_3CN$, 400 MHz) δ7.65-7.70 (m, 24H); $^{13}$C NMR ($CD_3CN$, 100 MHz) δ118.6, 125.4 (q, $J_{C-F}$=271 Hz), 129.9 (q, $J_{C-F}$=31.5 Hz), 135.6, 162.6 (q, $J_{B-C}$=48.6 Hz); $^{19}$F NMR ($CD_3CN$) δ−63.1. Anal. Calcd. for $C_{64}H_{40}BCaF_{48}O_8$: C, 40.23; H, 2.11. Found: C, 40.23; H, 2.30.

$Ba[B(3,5-CF_3C_6H_3)_4]_2 \cdot /H_2O$

Pale brown powder. $^1$H NMR ($CD_3CN$, 400 MHz) δ 77.65-7.70 (m, 24H); $^{19}$F NMR ($CD_3CN$) δ −63.1. Anal. Calcd. For $C_{64}H_{38}BBaF_{24}O_7$: C, 38.63; H, 1.92. Found: C, 38.65; H, 2.08.

$Sr[B(C_6F_5)_4]_2$

White powder. $^{19}$F NMR ($CD_3CN$) δ−168.3, −163.8 (t, J=24.6 Hz), −133.7.

Examples 1 to 11, Comparative Examples 1 and 2

As shown in Table 1, in Examples 1 to 11, ε-caprolactone was manufactured from commercially available cyclohexanone with various borate salts functioning as the catalyst by a Baeyer-Villiger oxidation reaction using hydrogen peroxide. In Comparative Examples 1 and 2, by using TsOH and $Sc(OTf)_3$, respectively, as the catalyst, ε-caprolactone was manufactured in a manner similar to that described above. Details of the catalysts and reaction conditions used in the above Examples and Comparative Examples are as shown in Table 1. In addition, besides ε-caprolactone, this reaction also produced a hydroxycarboxylic acid by hydrolysis of this lactone and a spiro-bisperoxide by dimerization of a Criegee intermediate (see *4 shown under Table 1) which was a reaction intermediate of a Baeyer-Villiger oxidation reaction. In Table 1, the conversion rate from cyclohexanone to the reaction products and the yield of each product are shown. In addition, the conversion rate of cyclohexanone and the yield of each product shown in Table 1 were calculated by $^1$H NMR analysis using a small amount sample taken from the reaction solution.

anhydride, and the solvent was removed by an evaporator, a product (47 mg, 0.41 mmol, isolated yield: 82%) was obtained by silica gel chromatography (developing solvent: hexane-Et$_2$O). The physical properties, the retention time of TLC, and the chemical shift of $^1$H NMR of this product coincided with those of commercially available ε-caprolactone. In addition, in the other Examples and Comparative Examples, the reaction was carried out in accordance with that in Example 4.

TABLE 1

| Catalyst | Reaction condition | Conversion rate % | Yield, % [X1] Lactone | Acid | Peroxide |
|---|---|---|---|---|---|
| Example 1 | LiB(3,5-CF$_3$C$_6$H$_3$)$_4$, 1 mol % | DCE, 70° C., 23 h | >99 | 68 | 14 | 18 |
| Example 2 | NaB(3,5-CF$_3$C$_6$H$_3$)$_4$, 1 mol % | DCE, 70° C., 4 h | 96 | 73 | 14 | 9 |
| Example 3 | Ca[B(3,5-CF$_3$C$_6$H$_3$)$_4$]$_2$, 1 mol % | DCE, 70° C., 1.5 h | >99 | 84 | 16 | trace |
| Example 4 | Sr[B(3,5-CF$_3$C$_6$H$_3$)$_4$]$_2$, 1 mol % | DCE, 70° C., 2 h | >99 | 88(82)[X2] | 10 | 2 |
| Example 5 | Sr[B(3,5-CF$_3$C$_6$H$_3$)$_4$]$_2$, 0.1 mol % | DCE, 70° C., 2 h | >99 | 77 | 14 | 9 |
| Example 6 | Ba[B(3,5-CF$_3$C$_6$H$_3$)$_4$]$_2$, 1 mol % | DCE, 70° C., 4 h | >99 | 75 | 15 | trace(10)[X3] |
| Example 7 | LiB(C$_6$F$_5$)$_4$, 1 mol % | DCE, 70° C., 2 h | >99 | 77 | 15 | 8 |
| Example 8 | Sr[B(C$_6$F$_5$)$_4$]$_2$ 1 mol % | DCE, 70° C., 30 min | >99 | 84 | 14 | 2 |
| Example 9 | Ph$_3$CB(C$_6$F$_5$)$_4$, 1 mol % | DCE, 70° C., 20 min | >99 | 74 | 26 | trace |
| Example 10 | Sr[B(3,5-CF$_3$C$_6$H$_3$)$_4$]$_2$, 1 mol % | DCB, 70° C., 1 h | >99 | 77 | 15 | 8 |
| Example 11 | Sr[B(3,5-CF$_3$C$_6$H$_3$)$_4$]$_2$, 1 mol % | Toluene, 70° C.,6 h | ca.80 | ca.50 | ca.20 | ca.10 |
| Comparative Example 1 | TsOH, 1 mol % | DCE, 70° C., 24 h | Low conversion rate and undesirable reaction | | | |
| Comparative Example 2 | Sc(OTf)$_3$, 1 mol % | DCE, 70° C., 24 h | 78 | 39 | 39 | trace |

[X1] The yield is calculated by $^1$H NMR analysis.
[X2] The value inside the parentheses indicates an isolated yield.
[X3] The value inside the parentheses indicates other components.
[X4] The peroxide is a dimer of a Criegee intermediate shown below.

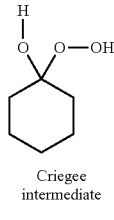

Criegee intermediate

As a representative example, a detailed experimental procedure of Example 4 will be described. To a 1,2-dichloroethane (10 ml) solution of cyclohexanone (50 mg, 0.5 mmol) and Sr[B(3,5-CF$_3$C$_6$H$_3$)$_4$]$_2$·10H$_2$O (10 mg, 0.005 mmol), hydrogen peroxide water at a concentration of 30% (57 μl, 0.55 mmol) was added, and a reaction container was placed in an oil bath at 70° C. In this reaction, since the by-production of hydroxycarboxylic acid caused by hydrolysis of ε-caprolactone thus produced was a serious problem, as the reaction solvent, 1,2-dichloroethane was only used instead of using a mixed solvent of 1,2-dichloroethane and water (in the reaction system, water contained in the hydrogen peroxide water was only present). After 2 hours from the start of the reaction, the reaction container was recovered from the oil bath, cooled to 0° C., and quenched with an aqueous NaHSO$_3$ solution. A water layer was extracted twice with Et$_2$O, and an obtained organic layer was washed with water and a saline solution. After the organic layer thus obtained was dried with Na$_2$SO$_4$ As apparent from the results of Examples 1 to 6 shown in Table 1, as the metal species of the borate salt used as the catalyst, all alkali metals and alkaline earth metals showed excellent results. Among those mentioned above, Ca and Sr are particularly excellent in reaction activity and lactone selectivity. In addition, as shown in Example 5, even when the catalyst amount was decreased from 1 to 0.1 percent by mole, the reaction efficiently progressed. Furthermore, as shown in Examples 7 to 9, when a counter-anion of the catalyst was changed from tetrakis(3,5-bis(trifluoromethyl)phenyl)borate to tetrakis(pentafluorophenyl)borate, the reaction activity was significantly improved. In addition, as shown in Examples 10 and 11, when the solvent was investigated, although the result obtained using 1,4-dichlorobutane was excellent similar to that of 1,2-dichloroethane, the reaction activity was slightly degraded when toluene was used. In addition, although not shown in Table 1, when the reaction temperature in Example 4 was decreased to 50° C. or to room temperature (25° C.), the reaction rate decreased, and at the same time, the amount of the produced spiro-bisperoxide tended to increase. In addition, although toric acid, which was a protonic acid, was used as the catalyst in Comparative Example 1, and Sc(OTf)$_3$, which was a Lewis acid, was used as the catalyst in Comparative Example 2, in both cases, the reaction activity was low, and the yield of lactone was not satisfactory.

By the way, the appearance and spectral data of each product are shown below.

Lactone (ε-Caprolactone)

Colorless liquid. TLC, $R_f$=0.11 (hexane-EtOAc=4:1); $^1$H NMR (CDCl$_3$, 400 MHz) δ 1.76-1.87 (m, 6H), 2.63-2.66 (m, 2H), 4.23-4.26 (m, 2H).

Hydroxycarboxylic Acid (6-Hydroxycaproic Acid)

Colorless solid. $^1$H NMR (CDCl$_3$, 400 MHz) δ 1.41 (m, 2H), 1.63 (m, 4H), 2.36 (t, J=7.4 Hz, 2H), 3.65 (t, J=6.5 Hz, 2H); $^{13}$C NMR (CDCl$_3$, 100 MHz) δ 24.4, 25.1, 31.9, 33.9, 62.3, 178.8.

Spiro-bisperoxide
(7,8,15,16-tetraoxadispiro[5.2.5.2]hexadecane

White solid. TLC, $R_f$=0.67 (hexane-EtOAc=4:1); $^1$H NMR (CDCl$_3$, 400 MHz) δ 1.47 (bs, 4H), 1.57 (bs, 12H), 2.28 (bs, 4H).

Examples 12 to 23, Comparative Examples 3 to 6

As shown in Table 2, in Examples 12 to 23, an ε-caprolactone corresponding to commercially available 4-tert-butylcyclohexanone was manufactured with various borate salts functioning as the catalyst by a Baeyer-Villiger oxidation reaction using hydrogen peroxide. The catalyst was not used in Comparative Example 3, NaBF$_4$, NaBPh$_4$, and LiNTf$_2$ were used as the catalysts in Comparative Examples 4 to 6, respectively, and the same ε-caprolactone as described above was manufactured in a manner similar to that described above. In the above Examples and Comparative Examples, the catalysts and reaction conditions shown in Table 2 were used, and the reaction was carried out in accordance with that in Example 4. In addition, in this reaction, besides the ε-caprolactone, a spiro-bisperoxide was also produced. In Table 2, the conversion rate from the cyclohexanone to the reaction products and the yield of each product are shown. In addition, the conversion rate and the yield of each product shown in Table 2 were calculated by $^1$H NMR analysis using a small amount sample taken from the reaction solution.

TABLE 2

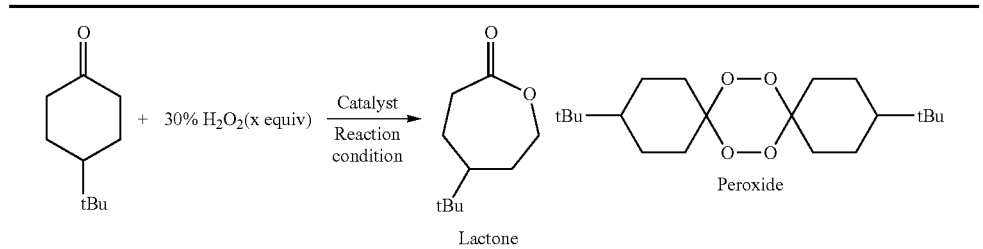

| | x | Catalyst | Reaction condition | Conversion rate % | Yield % [X.1] |
|---|---|---|---|---|---|
| Example 12 | 2.0 | NaB(3,5-CF$_3$C$_6$H$_3$)$_4$, 5 mol % | DCE, 70° C., 24 h | >99 | 73 (27) |
| Example 13 | 2.0 | NaB(3,5-CF$_3$C$_6$H$_3$)$_4$, 5 mol % | DCE-H$_2$O(2:1), 70° C., 17 h | 93 | 89 [X.2](0) |
| Example 14 | 2.0 | NaB(3,5-CF$_3$C$_6$H$_3$)$_4$, 5 mol % | Toluene-H$_2$O(2:1), 70° C., 17 h | 45 | 45 (0) |
| Example 15 | 2.0 | NaB(3,5-CF$_3$C$_6$H$_3$)$_4$, 5 mol % | CH$_3$CN—H$_2$O(2:1), 70° C., 26 h | 16 | 16 (0) |
| Example 16 | 2.0 | NaB(3,5-CF$_3$C$_6$H$_3$)$_4$, 5 mol % | DCE-H$_2$O(10:1), 70° C., 3 h | >99 | >95 (<5) |
| Example 17 | 2.0 | LiB(3,5-CF$_3$C$_6$H$_3$)$_4$, 1 mol % | DCE-H$_2$O(10:1), 70° C., 4 h | 90 | 90 [X.2](0) |
| Example 18 | 2.0 | NaB(3,5-CF$_3$C$_6$H$_3$)$_4$, 1 mol % | DCE-H$_2$O(10:1), 70° C., 4 h | 90 | 90 (0) |
| Example 19 | 2.0 | KB(3,5-CF$_3$C$_6$H$_3$)$_4$, 1 mol % | DCE-H$_2$O(10:1), 70° C., 4 h | 92 | 84 (8) |
| Example 20 | 2.0 | Ca[B(3,5-CF$_3$C$_6$H$_3$)$_4$]$_2$, 1 mol % | DCE-H$_2$O(10:1), 70° C., 3 h | 99 | 99 (0) |
| Example 21 | 1.1 | LiB(3,5-CF$_3$C$_6$H$_3$)$_4$, 1 mol % | DCE-H$_2$O(10:1), 50° C., 67 h | 89 | 85 (4) |
| Example 22 | 1.1 | LiB(C$_6$F$_5$)$_4$, 1 mol % | DCE-H$_2$O(10:1), 50° C., 24 h | 90 | 90 (0) |
| Example 23 | 1.1 | Ph$_3$CB(C$_6$F$_5$)$_4$, 1 mol % | DCE, 50° C., 20 h | 94 | 94 (0) |
| Comparative Example 3 | 2.0 | — | DCE, 70° C., 24 h | <5 | — |
| Comparative Example 4 | 2.0 | NaBF$_4$, 5 mol % | DCE-H$_2$O(10:1), 70° C., 24 h | <5 | — |
| Comparative Example 5 | 2.0 | NaBPh$_4$, 5 mol % | DCE-H$_2$O(10:1), 70° C., 24 h | <5 | — |
| Comparative Example 6 | 2.0 | LiNTf$_2$, 5 mol % | DCE-H$_2$O(10:1), 70° C., 48 h | 63 | 48 (15) |

[X.1] The value outside the parentheses indicates the yield of lactone, the value inside the parentheses indicates the yield of peroxide (other than [X.2], the yield is calculated by $^1$H NMR analysis).
[X.2] indicates the isolated yield.

As apparent from the results of Comparative Example 3 shown in Table 2, this reaction did not progress without catalyst. In Example 12, when the reaction was carried out in 1,2-dichloroethane with NaB(3,5-CF$_3$C$_6$H$_3$)$_4$ as the catalyst at a concentration of 5 percent by mole to the reactive substrate and 2 mole equivalents of hydrogen peroxide, the lactone was obtained at a yield of 73%, and the spiro-bisperoxide, which was a by-product, was obtained at a yield of 27%. In Example 13, when a mixed solvent of 1,2-dichloroethane and water at a volume ratio of 2:1 was used as the reaction solvent, the yield of the lactone was increased to 89%. In Examples 14 and 15, when toluene and acetonitrile were used, respectively, instead of 1,2-dichloroethane used in Example 13, although the reaction activity was decreased, the lactone was selectively obtained. In these Examples 14 and 15, although the progress of the reaction was slow, compounds other than the lactone were not produced; hence, when the reaction time is increased, the yield of the lactone is expected to increase. In Example 16, when a mixed solvent of 1,2-dichloroethane and water at a volume ratio of 10:1 was used as the reaction solvent, the reaction activity was significantly improved as compared to that in Example 13, and the yield of the lactone was also improved.

In Examples 17 to 20, when the reaction was carried out in a reaction solvent similar to that in Example 16 with a metal borate (the metal species were Li, Na, K, and Ca, respectively) as the catalyst at a concentration of 1 percent by mole to the reactive substrate and 2 mole equivalents of hydrogen peroxide, preferable results were obtained in each Example such that the reactivity was high, the conversion rate was 90% or more, and the yield of the lactone was also 84% or more. Although the reaction results were not significantly different from each other by the metal species, if the reaction activities thereof were evaluated for comparison purpose, the order from high to low reaction activity was Ca, Li, Na, and K.

In Examples 21 to 23, when the reaction was carried out in a reaction solvent similar to that in Example 16 with a borate salt as the catalyst at a concentration of 1 percent by mole to the reactive substrate and 1.1 mole equivalents of hydrogen peroxide, preferable results were obtained in each Example such that the reactivity was high, the conversion rate was 89% or more, and the yield of the lactone was also 85% or more. In the borate salt used in Example 23, although the cation was a trityl cation, preferable results were obtained.

By the way, the appearance and spectral data of each product are shown below.

Lactone (5-tert-butyloxepan-2-one)

Colorless solid. TLC, R$_f$=0.35 (hexane-EtOAc=4:1); $^1$H NMR (CDCl$_3$, 400 MHz) δ 0.89(s, 9H), 1.25-1.40 (m 2H), 1.48-1.55 (m, 1H), 2.0-2.1 (m, 2H), 2.53-2.59 (m, 1H), 2.69-2.74 (m, 1H), 4.11-4.18 (m, 1H), 4.34 (ddd, J=1.9, 5.9, 12.8 Hz, 1H); $^{13}$C NMR (CDCl$_3$, 100 MHz) δ23.6, 27.3, 30.1, 32.3, 33.3, 50.6, 69.0, 177.8.

Spiro-bisperoxide (3,12-di-tert-butyl-7,8,15,16-tetraoxadispiro[5.2.5.2]hexadecane)

White solid. TLC, R$_f$=0.75 (hexane-EtOAc=4:1); $^1$H NMR (CDCl$_3$, 400 MHz) δ 0.86(bs, 18H), 1.05-1.12 (m, 2H), 1.20-1.32 (m, 4H), 1.41-1.51 (m, 4H), 1.74 (bs, 6H), 3.17 (bs, 2H); $^{13}$C NMR (CDCl$_3$, 100 MHz) δ 22.8, 23.1, 27.6, 29.7, 32.0, 32.3, 47.4, 47.5, 108.1.

Examples 24 to

In Examples 24 to 30, as shown in Chem. 1, lactones were synthesized from various cyclic ketones by a Baeyer-Villiger oxidation reaction using hydrogen peroxide. In Example 24, when 2-methylcyclohexanone, which was an asymmetric cyclic ketone, was used, a corresponding ε-caprolactone was obtained at a high yield with normal regioselectivity. In Example 25, when 4-isopropenylcyclohexanone, which was a cyclic ketone having a substituent with an olefinic bond, was used, a corresponding ε-caprolactone was obtained at a yield of 56%, and no epoxidation of the olefin was observed. In Example 26, when 4-hydroxycyclohexanone was used, a five-membered lactone having a hydroxyethyl group was obtained. In this case, it is construed that after a corresponding ε-caprolactone was formed, this lactone was obtained by rearrangement therefrom into a five-membered ring having a smaller ring strain. In Examples 27 to 29, when a five-membered ring ketone and a four-membered ring ketone were used, corresponding six-membered ring lactone and five-membered ring lactone were obtained at a high yield. In Example 30, when a condensed ring ketone having an olefinic bond inside the ring was used, a corresponding condensed ring lactone was obtained at a high yield with normal regioselectivity, and no epoxidation of the olefin was observed.

In addition, commercially available products were used for 2-methylcyclohexanone of Example 24 and cyclopentanone of Example 27, and starting raw materials of the other Examples were synthesized in accordance with the methods described in the literatures (*1 to 5 shown in Chem. 1).

[Chem. 1]

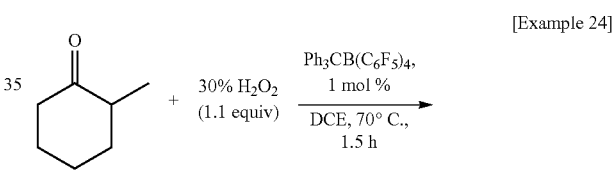

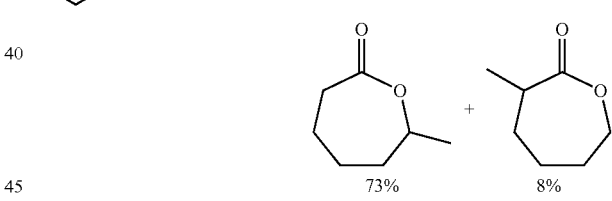

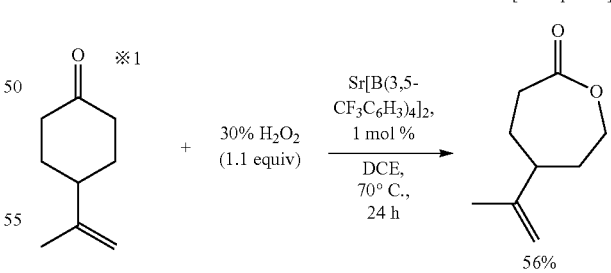

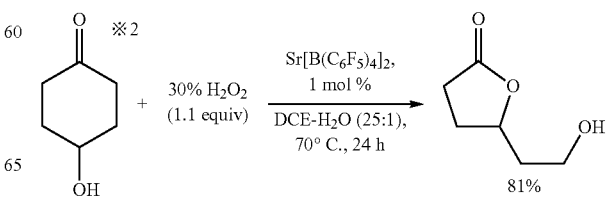

-continued

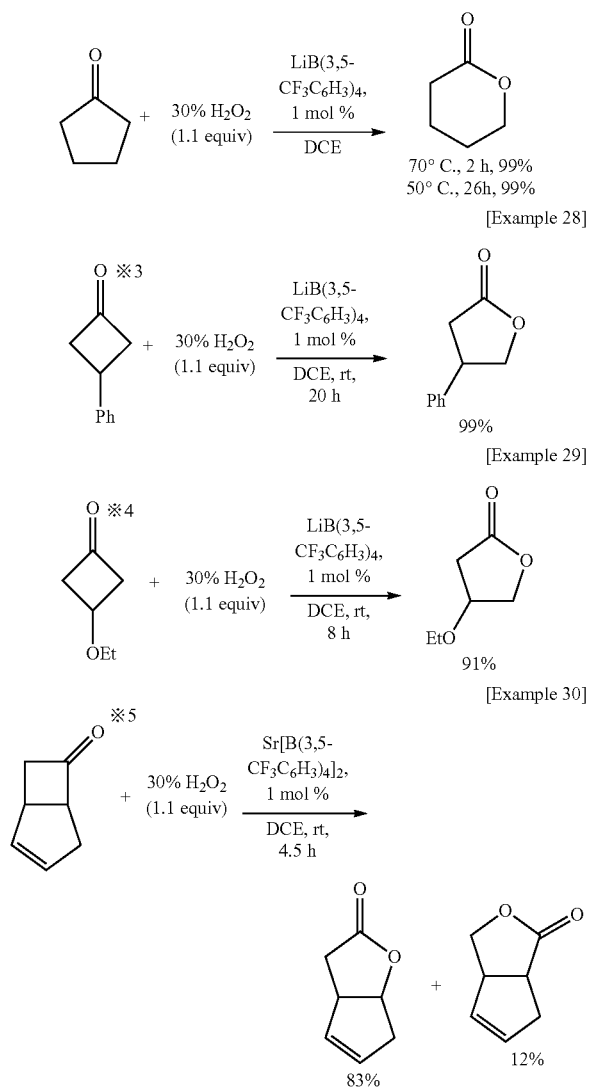

[Example 27]
[Example 28]
[Example 29]
[Example 30]

※ 1. (a) Jung, M. E.; McCombs, C. A. *Tetrahedron. Lett.* 1976, 34, 2935;
(b) Stevens, R.; Albizati, K. F.; *J. Org. Chem.* 1985, 50, 632.
※ 2. Seo, J. W.; Comninos, J. S.; Chi, D. Y.; Kim, D. W. Carlson, K. E.; Katzenellenbogen. J. A. *J. Med. Chem.* 2006, 49, 2496.
※ 3. Schmit, C.; Falmagne, J. B.; Escudero, J.; Vanlierde, H.; Ghosez, L. *Org. Synth.*, 1993, 8, 306.
※ 4. Matsuo, J.; Okuno, R.; Takeuchi, K.; Kawano, M.; Ishibashi, H. *Tetrahedron Lett.* 2010, 51, 3736.
※ 5. Grieco, P. A. *J. Org. Chem.* 1972, 37, 2363.

The appearance and spectral data of the products of each Example are shown below.

Major product of Example 24: Colorless oil. TLC, $R_f$=0.12 (hexane-EtOAc=4:1); $^1$H NMR (CDCl$_3$, 400 MHz) δ 1.36 (d, J=6.5 Hz, 3H), 1.50-1.74 (m, 3H), 1.82-2.02 (m, 3H), 2.53-2.74 (m, 2H), 4.39-4.52 (m, 1H).

Minor product of Example 24: Colorless oil. TLC, $R_f$=0.13 (hexane-EtOAc=4:1); $^1$H NMR (CDCl$_3$, 400 MHz) δ 1.21 (d, J=6.6 Hz, 3H), 1.45-1.81 (m, 4H), 1.88-2.03(m, 2H), 2.65-2.81 (m, 1H), 4.16-4.35 (m, 2H).

Product of Example 25: Colorless solid. TLC, $R_f$=0.12 (hexane-EtOAc=4:1); $^1$H NMR (CDCl$_3$, 400 MHz) δ 1.59-1.67 (m, 1H), 1.72 (s, 3H), 1.77-1.83 (m, 1H), 1.92-2.02 (m, 2H), 2.21-2.28 (m, 1H), 2.60-2.66 (m, 1H), 2.71-2.76 (m, 1H), 4.17-4.23 (m, 1H), 4.32-4.37 (m, 1H), 4.74 (s, 1H), 4.78 (s, 1H); $^{13}$C NMR (CDCl$_3$, 100 MHz) δ 20.7, 27.9, 33.5, 34.4, 48.2, 68.3, 110.6, 148.2, 176.1.

Product of Example 26: Colorless oil. TLC, $R_f$=0.22 (EtOAc); $^1$H NMR (CDCl$_3$, 400 MHz) δ 1.89-1.97 (m, 3H), 2.35-2.43 (m, 1H), 2.54-2.58 (m, 2H), 3.82-3.85 (m, 2H), 4.68-4.75 (m, 1H).

Product of Example 27: Colorless oil. TLC, $R_f$=0.13 (hexane-EtOAc=4:1); $^1$H NMR (CDCl$_3$, 400 MHz) δ 1.86-1.93 (m, 4H), 2.55 (t, J=6.9 Hz, 2H), 4.35 (t, J=6.9 Hz, 2H).

Product of Example 28: Colorless solid. TLC, $R_f$=0.37 (hexane-EtOAc=4:1); $^1$H NMR (CDCl$_3$, 400 MHz) δ 2.68 (dd, J=9.2, 17.4 Hz, 1H), 2.93 (dd, J=8.7, 17.4 Hz, 1H), 3.76-3.84 (m, 1H), 4.28 (dd, J=7.8, 9.2 Hz, 1H), 4.68 (dd, J=7.8, 9.2 Hz, 1H), 7.23-7.46 (m, 5H).

Product of Example 29: Colorless solid. TLC, $R_f$=0.1 (hexane-EtOAc=4:1); $^1$H NMR (CDCl$_3$, 400 MHz) δ1.22 (t, J=6.9, 3H), 2.58 (dd, J=17.9, 2.7 Hz, 1H), 2.68 (dd, J=17.9, 6.4 Hz, 1H), 3.49 (q, J=6.9 Hz, 2H), 4.25-4.29 (m, 1H), 4.34 (dd, J=10.1, 2.3 Hz, 1H), 4.38 (dd, J=10.1, 4.6 Hz, 1H); $^{13}$C NMR (CDCl$_3$, 100 MHz) δ15.1, 35.0, 64.6, 73.3, 74.3, 175.9.

Isolated mixture of major product (A) and minor product (B) of Example 30: Yellow oil. TLC, $R_f$=0.16 (hexane-EtOAc=4:1); $^1$H NMR (CDCl$_3$, 400 MHz) δ 2.45 (dd, J=18.3, 1.8 Hz, 1H, for A), 2.70-2.84 (m, 3H, for A, B), 3.14 (ddd, J=7.8, 7.8, 1.8 Hz, 1H, for B), 3.49-3.55 (m, 1H, for A), 3.57-3.63 (m, 1H, for B), 4.25 (dd, J=9.2, 1.4 Hz, 1H, for B), 4.43 (dd, J=9.2, 6.9 Hz, 1H, for B), 5.11-5.16 (m, 1H, for A), 5.57-5.61 (m, 1H, for A), 5.65-5.68 (m, 1H, for B), 5.78-5.82 (m, 1H, for A), 5.86-5.89 (m, 1H, for B); $^{13}$C NMR (CDCl$_3$, 100 MHz) δ 32.3(A), 36.5(B), 39.5(A), 41.7(B), 45.6(A), 46.4(B), 71.5(B), 83.1(A), 129.7(A), 130.7(B), 131.3(A), 132.4(B), 176.8(A), 181.0(B).

Examples 31 to 56, Comparative Examples 7 and 8

As shown in Table 3, in Example 31, δ-valerolactone was synthesized from cyclopentanone by a Baeyer-Villiger oxidation reaction only using a borate salt catalyst. In addition, in Examples 32 to 56, δ-valerolactone was synthesized from cyclopentanone by a Baeyer-Villiger oxidation reaction using a borate salt catalyst and a Brønsted acid promoter. The structures of the promoters used in Examples are shown in Table 4.

As a representative example of a Baeyer-Villiger oxidation reaction using the catalyst and the promoter, a detailed experimental procedure of Example 39 will be described. In addition, in the other Examples and Comparative Examples, the reaction was carried out in accordance with that in Example 39. To a 1,2-dichloroethane (10 ml) solution of cyclopentanone (84 mg, 1.0 mmol), Li[B(C$_6$F$_5$)$_4$].2.5Et$_2$O (10.4 mg, 0.01 mmol), and oxalic acid (4.6 mg, 0.05 mmol), hydrogen peroxide water at a concentration of 30% (115 μl, 1.1 mmol) was added, and a reaction container was placed in an oil bath at 50° C. After 6 hours from the start of the reaction, the reaction container was recovered from the oil bath, cooled to 0° C., and quenched with an aqueous NaHSO$_3$ solution. A water layer was extracted twice with Et$_2$O, and an obtained organic layer was washed with water and a saline solution. After the organic layer thus obtained was dried with Na$_2$SO$_4$ anhydride, and the solvent was removed by an evaporator, a product (94 mg, 0.94 mmol, isolated yield: 94%) was obtained by silica gel chromatography (developing solvent: hexane-Et$_2$O). The physical properties, the retention time of TLC, and the chemical shift of $^1$H NMR of this product coincided with those of commercially available δ-valerolactone. In Table 3, the conversion rates obtained after 1 hour and 4 hours from the start of the reaction are shown.

TABLE 3

Cyclopentanone + 30% H₂O₂ (1.1 equiv) → δ-valerolactone
Catalyst MBr₄ (xmol %), Promoter, Solvent (0.1 M)***, 50° C.

| Example | Catalyst M(BAr₄)ₙ | Promoter | Solvent | Conversion rate (%) * 1 h | 4 h |
|---|---|---|---|---|---|
| 31 | LiB(C₆F₅)₄ (1 mol %) | — | DCE | 8 | 60 |
| 32 | LiB(C₆F₅)₄ (1 mol %) | F₅—PhOH (5 mol %) | DCE | 10 | 67 |
| 33 | LiB(C₆F₅)₄ (1 mol %) | Catechol (5 mol %) | DCE | 17 | 75 |
| 34 | LiB(C₆F₅)₄ (1 mol %) | 3F-Catechol (5 mol %) | DCE | 25 | 83 |
| 35 | LiB(C₆F₅)₄ (1 mol %) | Cl₄-Catechol (5 mol %) | DCE | 46 | 89 |
| 36 | LiB(C₆F₅)₄ (1 mol %) | F₄-Catechol (5 mol %) | DCE | 39 | 92 |
| 37 | LiB(C₆F₅)₄ (1 mol %) | Acetic Acid (5 mol %) | DCE | 34 | 74 |
| 38 | LiB(C₆F₅)₄ (1 mol %) | Mandelic Acid (5 mol %) | DCE | 48 | 84 |
| 39 | LiB(C₆F₅)₄ (1 mol %) | Oxalic Acid (5 mol %) | DCE | 76 | 96 |
| 40 | LiB(C₆F₅)₄ (1 mol %) | Malonic Acid (5 mol %) | DCE | 61 | 93 |
| 41 | LiB(C₆F₅)₄ (1 mol %) | Succinic Acid (5 mol %) | DCE | 44 | 86 |
| 42 | LiB(C₆F₅)₄ (1 mol %) | Squaric Acid (5 mol %) | DCE | 78 | 96 |
| 43 | LiB(C₆F₅)₄ (1 mol %) | Salicyclic Acid (5 mol %) | DCE | 36 | 71 |
| 44 | LiB(C₆F₅)₄ (1 mol %) | Phthalic Acid (5 mol %) | DCE | 52 | 91 |
| 45 | LiB(C₆F₅)₄ (1 mol %) | BP (5 mol %) | DCE | 61 | 93 |
| 46 | LiB(C₆F₅)₄ (1 mol %) | F₄-Catechol (1 mol %) | DCE | 27 | 88 |
| 47 | LiB(C₆F₅)₄ (0.1 mol %) | F₄-Catechol (1 mol %) | DCE | 34 | 75 |
| 48 | Ca[B(C₆F₅)₄]₂ (0.01 mol %) | F₄-Catechol (0.05 mol %) | DCE | 21 | 59 |
| 49 | LiB(C₆F₅)₄ (1 mol %) | Oxalic Acid (1 mol %) | DCE | 74 | 97 |
| 50 | LiB(C₆F₅)₄ (0.1 mol %) | Oxalic Acid (1 mol %) | DCE | 50 | 85 |
| 51 | Ca[B(C₆F₅)₄]₂ (0.01 mol %) | Oxalic Acid (0.05 mol %) | DCE | 19 | 51 |
| 52 | LiB(C₆F₅)₄ (1 mol %) | — | Toluene | 49 | 68 |
| 53 | LiB(C₆F₅)₄ (1 mol %) | — | Benzene | 49 | 73 |
| 54 | LiB(C₆F₅)₄ (1 mol %) | F₄-Catechol (5 mol %) | Toluene | 62 | 88 |
| 55 | LiB(C₆F₅)₄ (1 mol %) | F₄-Catechol (5 mol %) | Benzene | 70 | 78 |
| 56 | LiB(C₆F₅)₄ (1 mol %) | Oxalic Acid (5 mol %) | Toluene | 72 | 79 |
| Comparative example **7 | | F₄-Catechol (5 mol %) | DCE | 0 | 0 |
| Comparative example **8 | | Oxalic Acid (5 mol %) | DCE | 0 | 0 |

* ¹H NMR analys
** Comparative example
***Concentration of reactive substrate to solvent

TABLE 4

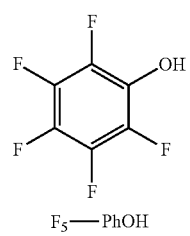

F₅—PhOH

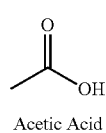

Acetic Acid

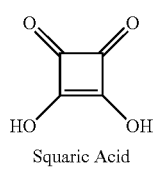

Squaric Acid

TABLE 4-continued

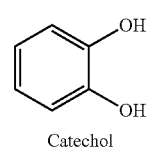

Catechol

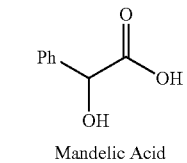

Mandelic Acid

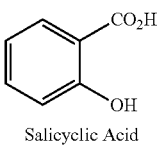

Salicyclic Acid

TABLE 4-continued

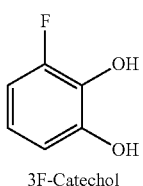

3F-Catechol

Oxalic Acid

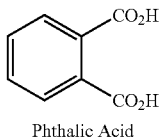

Phthalic Acid

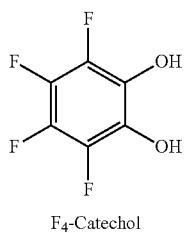

F$_4$-Catechol

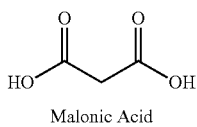

Malonic Acid

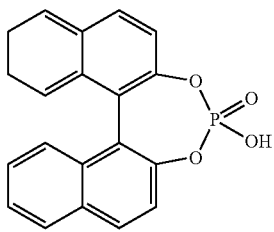

Binaphthyl hydrogen
phosphate (BP)

TABLE 4-continued

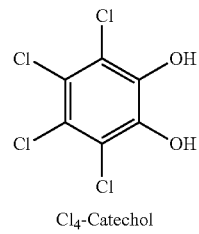 [SMILES: Oc1c(O)c(Cl)c(Cl)c(Cl)c1Cl]

Cl$_4$-Catechol

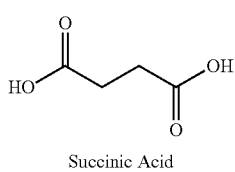

Succinic Acid

In Examples 32 to 45, the reaction was carried out in a DCE solvent using 1 percent by mole of LiB(C$_6$H$_5$)$_4$ as the catalyst and 5 percent by mole of the promoter. As a result, it was found that when a phenol (Examples 32 to 36), a carboxylic acid (Examples 37 to 44), and a phosphate diester (Example 45) were used as the promoter, compared to the results obtained in Example 31 in which no promoter was used, the reaction progressed faster, and the conversion rate was also increased. Among those mentioned above, tetrafluorocatechol (Example 36) and inexpensive oxalic acid (Example 39) were most effective. In addition, when the borate salt catalyst was not used, and the Brønsted acid used in Examples 36 or 39 was only used, the reaction did not progress at all (Comparative Examples 7 and 8).

In Examples 46 to 48 and 49 to 51, the reduction of the amounts of the catalyst and the promoter was investigated using tetrafluorocatechol and oxalic acid, respectively, as the promoter. As a result, the amount of the catalyst and that of the promoter could be reduced to 0.01 and 0.05 percent by mole, respectively (Examples 48 and 51).

In Examples 52 to 56, the effect of the promoter was investigated in a manner similar to that described above using toluene or benzene as the solvent. As a result, compared to the results of Examples 52 and 53 in which the promoter was not used, it was found that in Examples 54 to 56 in which the promoter was used, the activation effect could be obtained by the promoter.

Examples 57 to 76

As shown in Tables 5 and 6, the Baeyer-Villiger oxidation reaction was investigated using various reactive substrates. As the catalyst, a borate salt of Li or Ca was used. In general, although the catalytic activity of a Ca borate salt was higher, since a Li borate salt was a commercially available product, and the amount thereof to be used was small due to its low molecular weight, the Li borate salt was first used (Examples 57, 58, 66 to 71, and 73). However, when the Li borate salt was not sufficient depending on the reactive substrate, and the chemical yield of the product was low, the Ca borate salt was used as the catalyst (Examples 59 to 65, 72, and 74 to 76).

TABLE 5
| Example | Reaction formula and reaction condition |
|---|---|
| 57 | 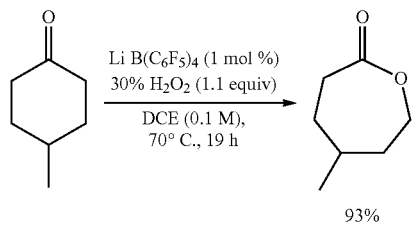 |
| 58 | 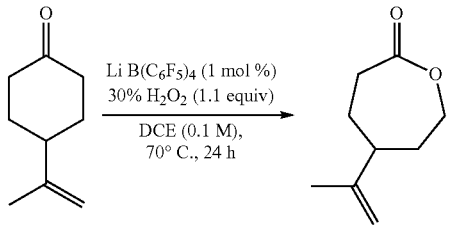 |
| 59 | 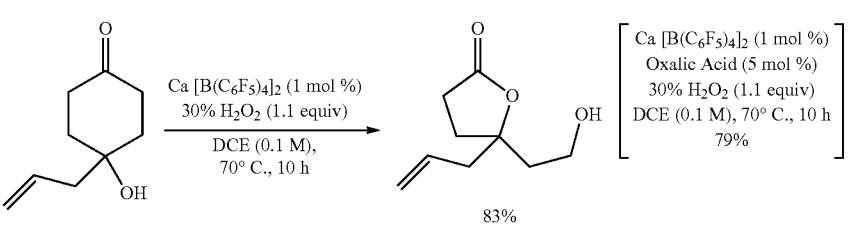 |
| 60 | 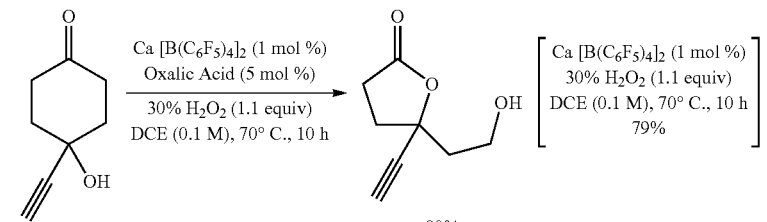 |
| 61 | 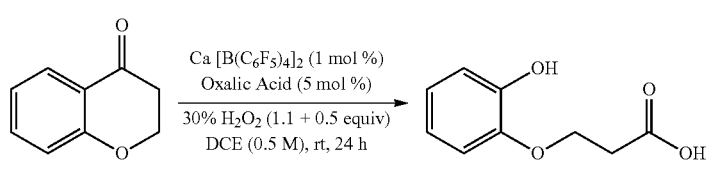 |
| 62 | 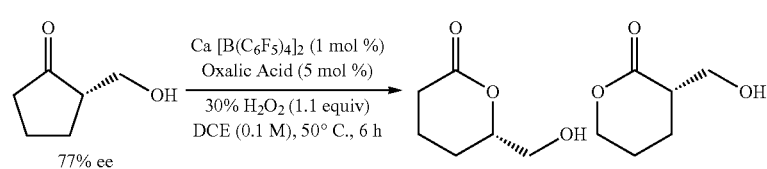 |
| 63 | 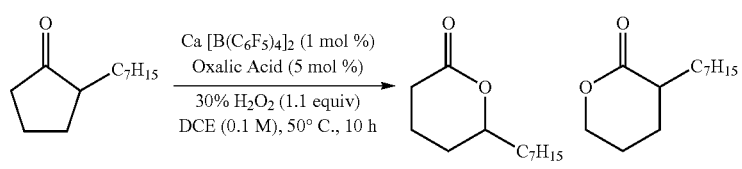 |

TABLE 5-continued

| Example | Reaction formula and reaction condition |
|---|---|
| 64 | Norcamphor + Ca[B(C$_6$F$_5$)$_4$]$_2$ (1 mol %), Oxalic Acid (5 mol %), 30% H$_2$O$_2$ (1.1 equiv), DCE (0.1 M), rt, 22 h → lactone (82%) + diketone (10%) |
| 65 | Camphor + Ca[B(C$_6$F$_5$)$_4$]$_2$ (1 mol %), Oxalic Acid (5 mol %), 30% H$_2$O$_2$ (1.1 equiv), DCE (0.1 M), 50° C., 18 h → lactone (72%) + diketone (6%) |
| 66 | 3-ethoxycyclobutanone + Li B(C$_6$F$_5$)$_4$ (1 mol %), Oxalic Acid (5 mol %), 30% H$_2$O$_2$ (1.1 equiv), DCE (0.5 M), rt, 8 h → 4-ethoxy-γ-butyrolactone (99%) |

TABLE 6

| Example | Reaction formula and reaction condition |
|---|---|
| 67 | 3-hydroxycyclobutanone + Li B(C$_6$F$_5$)$_4$ (1 mol %), 30% H$_2$O$_2$ (1.1 equiv), DCE (0.2 M), rt, 9 h → 4-hydroxy-γ-butyrolactone (99%) |
| 68 | 3-methyl-3-phenylcyclobutanone + Li B(C$_6$F$_5$)$_4$ (1 mol %), Oxalic Acid (5 mol %), 30% H$_2$O$_2$ (1.1 equiv), DCE (0.5 M), rt, 1.5 h → lactone (99%) |
| 69 | bromohydroxy bicyclic ketone + Li B(C$_6$F$_5$)$_4$ (1 mol %), Oxalic Acid (5 mol %), 30% H$_2$O$_2$ (1.1 equiv), DCE (0.2 M), rt, 2 h → lactone (80%) + regioisomer (14%) |

TABLE 6-continued

| Example | Reaction formula and reaction condition |
|---|---|
| 70 | Li B(C$_6$F$_5$)$_4$ (1 mol %), 30% H$_2$O$_2$ (1.1 equiv), DCE (0.2 M), rt, 24 h — 72% and 12% |
| 71 | Li B(C$_6$F$_5$)$_4$ (1 mol %), Oxalic Acid (5 mol %), 30% H$_2$O$_2$ (1.1 equiv), DCE (0.2 M), rt, 1 h — 83% and 13% |
| 72 | Ca [B(C$_6$F$_5$)$_4$]$_2$ (1 mol %), Oxalic Acid (5 mol %), 30% H$_2$O$_2$ (1.1 equiv), DCE (0.1 M), 50° C., 6 h — 63% and 24% |
| 73 | Li B(C$_6$F$_5$)$_4$ (1 mol %), 30% H$_2$O$_2$ (2.2 equiv), DCE (0.2 M), 50° C., 55 h — 59% |
| 74 | Ca [B(C$_6$F$_5$)$_4$]$_2$ (1 mol %), Oxalic Acid (5 mol %), 30% H$_2$O$_2$ (1.1 equiv), DCE (0.1 M), 50° C., 6 h — 80% |
| 75 | Ca [B(C$_6$F$_5$)$_4$]$_2$ (1 mol %), Oxalic Acid (5 mol %), 30% H$_2$O$_2$ (1.1 equiv), DCE (0.1 M), 50° C., 3 h — 83% and 10% |
| 76 | Ca [B(C$_6$F$_5$)$_4$]$_2$ (1 mol %), Oxalic Acid (5 mol %), 30% H$_2$O$_2$ (1.1 equiv), DCE (0.1 M), 50° C., 3 h — 88% and 12% |

Although the effect of addition of oxalic acid as the promoter was observed in all the reactive substrates, in oxidation of a six-membered ring aliphatic cyclic ketone, the reaction rate thereof was increased, but the hydrolysis of a produced lactone was also facilitated by the promoter. Hence, as a result, in the above case, the yield was not significantly improved. Accordingly, in Examples 57 and 58, the cases in which oxalic acid was not used were shown by way of example. Although the reactive substrate of Example 58 had an olefinic portion, this olefinic portion was not oxidized.

In Examples 59 and 60, when 4-hydroxycyclohexanone was used as the reactive substrate, a corresponding ε-caprolactone was first produced and was then rearranged into a five-membered ring having a small ring strain at a high yield. Although those reactive substrates had a carbon-carbon double bond and a carbon-carbon triple bond, those portions were not oxidized. In addition, in Table 5, although the result of Example 59 in which the promoter was not used was shown by way of example, the result obtained by using oxalic acid as the promoter was shown in the parentheses. In addition, although the result of Example 60 in which oxalic acid was used as the promoter was shown by way of example, the result obtained without using the promoter was shown in the parentheses.

In Example 61, when 4-chromanone was used as the reactive substrate, a produced lactone was hydrolyzed, and a corresponding hydroxycarboxylic acid was obtained.

In Example 62, when an optically-active cyclopentanone having an asymmetric point at the α position of the ketone was used as the reactive substrate, no racemization progressed at all, and a produced lactone retained its optical yield as it was. In this Example 62 and in Examples 63 to 65, although a reactive substrate in which two types of rearrangement were to be carried out from a Criegee intermediate was used, a product was obtained with regioselectivity similar to that as it was.

In Examples 66 to 72, when a cyclobutanone derivative was used as the reactive substrate, a corresponding lactone was obtained at a high yield in each case. Among the above Examples, in Examples 69 and 70, although an unstable reactive substrate, which had a halogen group at one carbon and a hydroxy group or a siloxy group at the carbon adjacent thereto and which was liable to form an epoxy ring, was used, no epoxidation occurred.

In Example 73, when a chain ketone was used as the reactive substrate, a corresponding chain ester was obtained at a high yield. In Example 74, when a benzaldehyde, which was an aromatic aldehyde, was used as the reactive substrate, a corresponding formate was hydrolyzed in the system, and as a result, a corresponding phenol was obtained at a high yield.

In Examples 75 and 76, when a cyclic ketone having a silyl group at the β position was used as the reactive substrate, a product produced by rearrangement of the α-carbon at the silyl side was obtained at a high selectivity, and at the same time, since β elimination reaction of a produced lactone occurred in the system, a corresponding alkenoic acid was obtained at a very high yield. Although the influence of a silyl group at the β position to the regioselectivity in a Baeyer-Villiger reaction has already been reported, a corresponding lactone was obtained by a related method (Hudrlik, et al. J. Am. Chem. Soc. 1980, vol. 102, p 6894). For example, as shown in Chem. 2, in synthesis of (+)-sporochnol A by Kotsuki et al., a corresponding lactone was obtained from a cyclic ketone at a high yield through oxidation by a related method (using mCPBA); however, a key intermediate, that is, an alkenoic acid, was obtained by β elimination at an intermediate yield with an excessive amount of BF$_3$·Et$_2$O (Kotsuki et al., Org. Lett. 2010, vol. 12, p 1616). On the other hand, according to the method of the present invention, since the β elimination reaction is also likely to progress, such a highly useful alkenoic acid can also be synthesized at a high yield. In addition, in the method of the present invention, although β elimination of PhMe$_2$Si as the silyl group occurred, since synthesis of raw materials for Me$_3$Si was easier, and the elimination thereof was faster, Me$_3$Si was used in Examples 75 and 76.

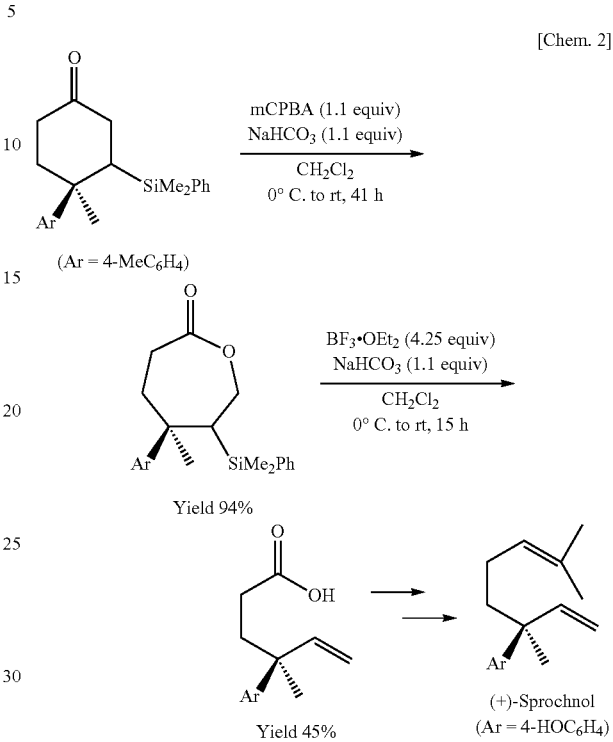

[Chem. 2]

The appearance and spectral data of the product of each Example are shown below.

Product of Example 57: Colorless oil. TLC, $R_f$=0.35 (hexane-EtOAc=4:1); $^1$H NMR (CDCl$_3$, 400 MHz) δ 1.00 (d, J=6.9 Hz, 3H), 1.29-1.44 (m, 1H), 1.44-1.55 (m, 1H), 1.84-1.98 (m, 3H), 2.56-2.72 (m, 2H), 4.18 (dd, J=12.8, 10.6 Hz, 1H), 4.29 (dd, J=1.8, 6.0 Hz, 1H); $^{13}$C NMR (CDCl$_3$, 100 MHz) δ 22.0, 30.6, 33.1, 35.1, 37.1, 68.0, 176.0.

Product of Example 58: colorless solid. The same product as that of Example 25.

Product of Example 59: Colorless oil. TLC, $R_f$=0.43 (EtOAc only); $^1$H NMR (CDCl$_3$, 400 MHz) δ 1.54 (bs, 1H), 1.92-2.04 (m, 2H), 2.15 (t, J=8.7 Hz, 2H), 2.42-2.50 (m, 2H), 2.60 (ddd, J=8.7, 8.7, 3.2 Hz, 2H), 3.78-3.90 (m, 2H), 5.18-5.22 (m, 2H), 5.73-5.83 (m, 1H); $^{13}$C NMR (CDCl$_3$, 100 MHz) δ 29.0, 30.7, 41.2, 43.6, 58.2, 87.5, 120.3, 131.7, 177.0.

Product of Example 60: Colorless oil. TLC, $R_f$=0.5 (EtOAc only); $^1$H NMR (CDCl$_3$, 400 MHz) δ 1.80 (brs, 1H), 2.11-2.23 (m, 2H), 2.28-2.38 (m, 1H), 2.50-2.63 (m, 2H), 2.69 (s, 1H), 2.76-2.85 (m, 1H), 3.90-4.04 (m, 2H); $^{13}$C NMR (CDCl$_3$, 100 MHz) δ 28.5, 36.1, 42.9, 59.0, 75.8, 80.2, 81.8, 175.7.

Product of Example 61: White solid. TLC, $R_f$=0.4 (EtOAc only); $^1$H NMR (CDCl$_3$, 400 MHz) δ 2.90 (t, J=6.0 Hz, 2H), 4.28 (t, J=6.0 Hz, 2H), 6.15 (brs, 1H), 6.81-6.86 (m, 1H), 6.92-6.97 (m, 3H); $^{13}$C NMR (CD$_3$CN, 100 MHz) δ 34.5, 66.2, 115.5, 116.2, 120.9, 123.3, 147.0, 147.9, 174.0.

Major product of Example 62: Colorless oil. TLC, $R_f$=0.18 (EtOAc only); $^1$H NMR (CDCl$_3$, 400 MHz) δ 1.70-1.75 (m, 1H), 1.86-2.00 (m, 4H), 2.44-2.52 (m, 1H), 2.60-2.66 (m, 1H), 3.65-3.71 (m, 1H), 3.81 (ddd, J=12.4, 7.3, 3.2 Hz, 1H), 4.40-4.45 (m, 1H). $^{13}$C NMR (CDCl$_3$, 100 MHz) δ 18.5, 23.7, 29.7, 65.0, 81.2, 171.7.

Minor product of Example 62: Colorless oil. TLC, $R_f$=0.24 (EtOAc only); $^1$H NMR (CDCl$_3$, 400 MHz) δ 1.63-1.72 (m, 1H), 1.92-2.08 (m, 3H), 2.64-2.72 (m, 1H), 2.91 (dd, J=8.2, 5.0 Hz, 1H), 3.72-3.83 (m, 2H), 4.33-4.36 (m, 2H); $^{13}$C NMR (CDCl$_3$, 100 MHz) δ 21.3, 22.0, 42.0, 62.9, 68.8, 175.0.

Major product of Example 63: Colorless oil. TLC, $R_f$=0.21 (hexane-EtOAc=4:1); $^1$H NMR (CDCl$_3$, 400 MHz) δ 0.88 (t, J=6.9 Hz, 3H), 1.21-1.40 (m, 9H), 1.43-1.61 (m, 3H), 1.66-1.75 (m, 1H), 1.79-1.93 (m, 3H), 2.40-2.48 (m, 1H), 2.55-2.63 (m, 1H), 4.24-4.30 (m, 1H); $^{13}$C NMR (CDCl$_3$, 100 MHz) δ 14.1, 18.6, 22.7, 25.0, 27.8, 29.2, 29.4, 29.5, 31.8, 35.9, 80.7, 172.1.

Minor product of Example 63: Colorless oil. TLC, $R_f$=0.26 (hexane-EtOAc=4:1); $^1$H NMR (CDCl$_3$, 400 MHz) δ 0.88 (t, J=6.9 Hz, 3H), 1.23-1.40 (m, 9H), 1.44-1.59 (m, 1H), 1.84-1.95 (m, 3H), 2.05-2.14 (m, 1H), 2.41-2.49 (m, 1H), 4.25-4.35 (m, 2H); $^{13}$C NMR (CDCl$_3$, 100 MHz) δ 14.2, 22.1, 22.8, 24.7, 27.0, 29.3, 29.6, 31.3, 31.9, 39.7, 68.5, 174.9.

Major product of Example 64: Colorless oil. TLC, $R_f$=0.13 (hexane-EtOAc=4:1); $^1$H NMR (CDCl$_3$, 400 MHz) δ 1.60-1.81 (m, 2H), 1.87-2.05 (m, 4H), 2.12-2.23 (m, 1H), 2.46-2.56 (m, 2H), 2.69-2.76 (m, 1H), 4.87 (m, 1H).

Minor product of Example 64: Colorless oil. TLC, $R_f$=0.15 (hexane-EtOAc=4:1); $^1$H NMR (CDCl$_3$, 400 MHz) δ 1.70-1.81 (m, 2H), 1.89-2.03 (m, 4H), 2.47 (m, 1H), 2.93 (t, J=9.6 Hz, 1H), 4.12 (d, J=10.6 Hz, 1H), 4.32 (dd, J=10.6, 2.3 Hz, 1H).

Isolated mixture of major product (A) and minor product (B) of Example 65: White solid. TLC, $R_f$=0.16 (hexane-EtOAc=4:1); $^1$H NMR (CDCl$_3$, 400 MHz) δ 0.90 (s, 3H for A), 0.97 (s, 3H, for B), 1.09 (s, 3H, for B), 1.10 (s, 3H, for A), 1.17 (s, 3H, for B), 1.30 (s, 3H, for A), 1.33-1.47 (m, 2H, for A), 1.70-1.92 (m, 1H for A, 3H for B), 2.05-2.17 (m, 1H for A, 2H for B), 2.35 (d, J=17.4 Hz, 1H, for A), 2.59 (ddd, J=10.6, 2.3 Hz, 1H, for A), 2.89 (dd, J=17.9, 9.2 Hz, 1H, for A), 4.10 (d, J=10.6 Hz, 1H, for B), 4.47 (m, 1H, for B); $^{13}$C NMR (CDCl$_3$, 100 MHz) δ 14.3(B), 18.7(A), 20.0(B), 21.9(A), 22.5(B), 23.9(A), 24.7(B), 27.0(B), 30.2(A), 36.2(B), 36.7(B), 37.9(A), 38.5(A), 43.0(A), 44.6(B), 45.3(A), 74.2(B), 98.9(A), 175.3(B), 177.4(A).

Product of Example 66: colorless oil. The same product as that of Example 29.

Product of Example 67: colorless oil. TLC, $R_f$=0.1 (hexane-EtOAc=1:1); $^1$H NMR (CDCl$_3$, 400 MHz) δ 2.54 (d, J=17.8, 1H), 2.58 (brs, 1H), 2.77 (dd, J=17.9, 5.6 Hz, 1H), 4.32 (d, J=10.1 Hz, 1H), 4.43 (dd, J=10.5, 4.6 Hz, 1H), 4.71 (m, 1H).

Product of Example 68: Colorless solid. TLC, $R_f$=0.25 (hexane-EtOAc=4:1); $^1$H NMR (CDCl$_3$, 400 MHz) δ 1.53 (s, 3H), 2.68 (d, J=17.0 Hz, 1H), 2.92 (d, J=17.0, 1H), 4.42 (m, 2H), 7.18-7.40 (m, 5H); $^{13}$C NMR (CDCl$_3$, 100 MHz) δ 28.1, 42.1, 44.2, 78.5, 125.3, 127.3, 129.1, 144.4, 176.3.

Isolated mixture of major product (A) and minor product (B) of Example 69: White solid. TLC, $R_f$=0.38 (hexane-EtOAc=1:2); $^1$H NMR (CDCl$_3$, 400 MHz) δ 2.15-2.26 (m, 1H, for A, B), 2.59-2.69 (m, 2H, for A, B), 2.87 (dd, J=18.3, 11.4 Hz, 1H, for A), 3.18 (ddd, 10.1, 10.1, 2.3 Hz, for B), 3.32-3.38 (m, 1H, for A), 4.02-4.07 (m, 1H, for A, B), 4.29 (dd, 10.1, 3.7 Hz, 1H, for B), 4.46-4.56 (m, 1H for A, 2H for B), 5.16 (t, J=6.4 Hz, 1H); $^{13}$C NMR (CDCl$_3$, 100 MHz) δ 35.9(A), 36.1(B), 38.3(A), 42.3(B), 48.1(A), 48.5(B), 58.0(B), 58.3(A), 72.7(B), 79.3(B), 79.4(A), 84.7(A), 177.7(A), 181.0(B).

Major product of Example 70: White solid. TLC, $R_f$=0.28 (hexane-EtOAc=4:1); $^1$H NMR (CDCl$_3$, 400 MHz) δ 0.09 (s, 3H), 0.10 (s, 3H), 0.87 (s, 9H), 2.15 (d, J=15.6 Hz, 1H), 2.52-2.58 (m, 1H), 2.61 (dd, J=18.3, 4.1 Hz, 1H), 2.85 (dd, J=18.3, 11.9 Hz, 1H), 3.39 (m, 1H), 4.06 (m, 1H), 4.42 (m, 1H), 5.20 (t, J=7.3 Hz, 1H); $^{13}$C NMR (CDCl$_3$, 100 MHz) δ −4.9, 18.0, 25.7, 35.9, 39.1, 48.3, 58.9, 80.4, 84.0, 176.1.

Minor product of Example 70: White solid. TLC, $R_f$=0.36 (hexane-EtOAc=4:1); $^1$H NMR (CDCl$_3$, 400 MHz) δ 0.08 (s, 3H), 0.09 (s, 3H), 0.86 (s, 9H), 2.22 (d, J=13.0 Hz, 1H), 2.56-2.62 (m, 1H), 3.18 (t, J=9.6 Hz, 1H), 3.37 (ddd, J=9.6, 9.6, 3.6 Hz, 1H), 4.00 (m, 1H), 4.20 (dd, J=9.6, 4.1 Hz, 1H), 4.37 (m, 1H), 4.53 (t, J=9.6 Hz, 1H)); $^{13}$C NMR (CDCl$_3$, 100 MHz) δ −5.1, 17.9, 25.5, 36.9, 42.3, 48.6, 58.7, 72.5, 80.0, 179.6.

Isolated mixture of major product (A) and minor product (B) of Example 71: the same product as that of Example 30.

Major product of Example 72: White solid. TLC, $R_f$=0.17 (hexane-EtOAc=4:1); $^1$H NMR (CDCl$_3$, 400 MHz) δ 5.34 (s, 2H), 7.50 (d, J=7.8 Hz, 1H), 7.55 (t, J=7.3 Hz, 1H), 7.70 (t, J=7.3 Hz, 1H), 7.94 (d, J=7.8 Hz, 1H); $^{13}$C NMR (CDCl$_3$, 100 MHz) δ 69.8, 122.2, 125.8, 129.1, 134.1, 146.6, 171.2.

Minor product of Example 72: Colorless oil. TLC, $R_f$=0.36 (hexane-EtOAc=4:1); $^1$H NMR (CDCl$_3$, 400 MHz) δ 3.75 (s, 2H), 7.10-7.16 (m, 2H), 7.28-7.33(m, 2H); $^{13}$C NMR (CDCl$_3$, 100 MHz) δ 33.1, 110.9, 123.2, 124.2, 124.8, 129.0, 154.8, 174.2.

Product of Example 73: Colorless oil. TLC, $R_f$=0.73 (hexane-EtOAc=4:1); $^1$H NMR (CDCl$_3$, 400 MHz) δ 0.88-0.95 (m, 6H), 1.28-1.39 (m, 8H), 1.58-1.66 (m, 4H), 2.29 (t, J=7.4 Hz, 2H), 4.06 (t, J=6.4 Hz, 2H); $^{13}$C NMR (CDCl$_3$, 100 MHz) δ 14.0(2C), 22.5(2C), 24.8, 28.3, 28.6, 31.5, 34.5, 64.4, 173.9.

Product of Example 74: Yellow oil. TLC, $R_f$=0.32 (hexane-EtOAc=4:1); $^1$H NMR (CDCl$_3$, 400 MHz) δ 4.76 (brs, 1H), 6.75-6.79 (m, 2H), 7.17-7.21 (m, 1H); $^{13}$C NMR (CDCl$_3$, 100 MHz) δ 116.8, 125.8, 129.7, 154.2.

Major product of Example 75: Colorless oil. TLC, $R_f$=0.14 (hexane-EtOAc=4:1); $^1$H NMR (CDCl$_3$, 400 MHz) δ 1.20 (d, J=6.8 Hz, 3H), 1.48-1.57 (m, 1H), 1.77-1.86 (m, 1H), 2.08-2.14 (m, 2H), 2.46-2.55 (m, 1H), 5.00-5.03 (m 2H), 5.74-5.84 (m, 1H); $^{13}$C NMR (CDCl$_3$, 100 MHz) δ 16.9, 31.4, 32.6, 38.8, 115.4, 137.8, 182.8.

Minor product of Example 75: Colorless oil. TLC, $R_f$=0.30 (hexane-EtOAc=4:1); $^1$H NMR (CDCl$_3$, 400 MHz) δ 0.32 (s, 9H), 1.04-1.10 (m, 1H), 1.36 (d, J=6.4 Hz, 3H), 1.75-1.84 (m, 4H), 2.65 (dd, J=14.7, 6.0 Hz, 1H), 2.92 (dd, J=14.2, 6.8 Hz, 1H), 4.53-4.456 (m, 1H); $^{13}$C NMR (CDCl$_3$, 100 MHz) δ −2.4, 20.7, 21.9, 27.0, 35.8, 36.0, 75.6, 175.1.

Major product of Example 76: Colorless oil. TLC, $R_f$=0.1 (hexane-EtOAc=4:1); $^1$H NMR (CDCl$_3$, 400 MHz) δ 1.00 (s, 6H), 1.63-1.67 (m, 2H), 2.26-2.30 (m, 1H), 4.91-5.00 (m, 2H), 5.72 (dd, J=17.4, 11.0 Hz, 1H); $^{13}$C NMR (CDCl$_3$, 100 MHz) δ 26.6, 30.0, 36.3, 36.8, 111.8, 147.0, 181.0.

Minor product of Example 76: Colorless oil. TLC, $R_f$=0.23 (hexane-EtOAc=4:1); $^1$H NMR (CDCl$_3$, 400 MHz) d 0.14 (s, 9H), 1.00-1.09 (m, 1H), 1.07 (s, 3H), 1.09 (s, 3H), 1.67 (m, 2H), 2.52-2.67 (m, 2H), 4.12-4.18 (m, 1H), 4.22-4.28 (m, 1H); $^{13}$C NMR (CDCl$_3$, 100 MHz) d 0.3, 24.8, 29.8, 31.8, 34.0, 35.2, 45.5, 176.8.

The present application claims priority from Japanese Patent Application No. 2010-245944 filed on Nov. 2, 2010, the entire contents of which are incorporated in the present specification by reference.

Industrial Applicability

The present invention can be used primarily for pharmaceutical chemical industry. In particular, ε-caprolactone, which is a lactone, is useful as a synthetic intermediate of a biodegradable polymer and nylon-6.

The invention claimed is:

1. A method for manufacturing an ester from a ketone or an aldehyde, which is a reactive substrate, by a Baeyer-Villiger oxidation reaction using hydrogen peroxide,
   wherein $M(BAr_4)$ which is a borate salt, is used as a catalyst (M represents an alkali metal, an alkaline earth metal, or a triarylmethyl; four Ar's each represent an aryl having an electron withdrawing group and are identical to or different from each other; and n is the same number as the valence of M).

2. The method for manufacturing an ester according to claim 1,
   wherein Ar of the borate salt represents pentafluorophenyl or 3,5-bistrifluoromethylphenyl.

3. The method for manufacturing an ester according to claim 1,
   wherein the catalyst is used in an amount of 0.1 to 5 percent by mole with respect to that of the reactive substrate.

4. The method for manufacturing an ester according to claim 1
   wherein the reactive substrate has a carbon-carbon double bond, a carbon-carbon triple bond, a halogen group, a hydroxyl group, a silyl group, or a siloxy group.

5. The method for manufacturing an ester according to claim 1,
   wherein the reactive substrate comprises a cyclic ketone, a chain ketone, a chromanone, or an aromatic aldehyde.

6. The method for manufacturing an ester according to claim 1,
   wherein the method uses a Bronsted acid as a promoter.

7. The method for manufacturing an ester according to claim 6,
   wherein the promoter comprises a phenol having at least one OH group on its aromatic ring, a carboxylic acid, an oxocarbonic acid, a phosphate monoester, or a phosphate diester.

8. The method for manufacturing an ester according to Claim 6,
   wherein the promoter is tetrafluorocatechol or oxalic acid.

9. The method for manufacturing an ester according to claim 6,
   wherein the amount of the promoter to be used is 1 to 5 times in mole that of the catalyst.

* * * * *